US005670559A

United States Patent [19]
Zeng et al.

[11] Patent Number: 5,670,559
[45] Date of Patent: Sep. 23, 1997

[54] PRIMER SOLUTION COMPOSITION FOR DENTAL BONDING

[75] Inventors: Weiping Zeng; Masami Arata; Tsuyoshi Banba, all of Moriyama, Japan

[73] Assignee: Sun Medical Co., Ltd., Moriyama, Japan

[21] Appl. No.: 447,943

[22] Filed: May 23, 1995

[30] Foreign Application Priority Data

May 26, 1994  [JP]  Japan ................. 6-112448

[51] Int. Cl.$^6$ ............... C08L 33/02; C08K 3/10; A61K 6/083
[52] U.S. Cl. ........... 523/118; 524/413; 524/435; 524/781; 524/785; 433/228.1; 433/215
[58] Field of Search ............. 523/118; 524/413, 524/781, 435, 785; 433/228.1, 215

[56] References Cited

U.S. PATENT DOCUMENTS

| | | | |
|---|---|---|---|
| 4,952,613 | 8/1990 | Hosoda | 523/109 |
| 5,252,629 | 10/1993 | Imai et al. | 523/118 |

FOREIGN PATENT DOCUMENTS

| | | |
|---|---|---|
| 5310524 | 11/1993 | Japan . |
| 5339118 | 12/1993 | Japan . |
| 0624928 | 2/1994 | Japan . |
| 0789821 | 4/1995 | Japan . |
| 2256875 | 12/1992 | United Kingdom . |

OTHER PUBLICATIONS

Database WPI, Week 9409 Derwent Publications Ltd., London, GB; AN 94–071806 & JP–A–06 024 928 (Mitsui Petrochem Ind Co. Ltd), 1 Feb. 1994.

Database WPI, Week 9351, Derwent Publications Ltd., London, GB; AN 93–410752, & JP–A–05 310 524 (Imai Y), 22 Nov. 1993.

*Primary Examiner*—Andrew E.C. Merriam
*Attorney, Agent, or Firm*—Sherman and Shalloway

[57] ABSTRACT

A primer composition for the treatment of a tooth surface, which comprises a) at least one metal compound selected from the group consisting of an iron compound, a copper compound and a cobalt compound, b) a polymerizable monomer having an acidic group, and c) water or water and an organic solvent miscible with water; and a method of forming an adhesive layer on a tooth surface, which comprises applying this primer composition to the tooth surface and then applying a curable composition containing trialkylborane or partial oxide thereof and a polymerizable monomer. According to the present invention, both the enamel and the dentin of a tooth can be simultaneously surface-treated without acid treatment or washing with water, and adhesion dental treatment can be reliably carried out by a simple operation without causing pains on a patient.

17 Claims, No Drawings

PRIMER SOLUTION COMPOSITION FOR DENTAL BONDING

DETAILED DESCRIPTION OF THE INVENTION

The present invention relates to a primer composition which can be applied to the simultaneous surface-treatment of enamel and dentin of a tooth by a simple operation and can prevent stimulus to dental pulp without widely opening dental tubules in dentin, and a method of forming an adhesive layer on a tooth surface by consecutively applying the primer composition and a curable composition to the tooth surface.

In the field of dental treatment, it is required to firmly bond a tooth and a material for restoring the tooth (e.g., a polymer substance, a metal or a ceramic) to each other, and various adhesives therefor have been proposed.

The above adhesives are generally composed of three components such as (1) a polymerizable monomer, (2) a polymerization catalyst or a polymerization initiator and (3) a filler.

Typical examples of the above adhesives include
an adhesive composition comprising
  (1) (meth)acrylic acid ester as a polymerizable monomer,
  (2) a mixture of benzoyl peroxide and an aromatic tertiary amine as a polymerization initiator or a catalyst component prepared by adding a sulfinic acid salt to this mixture, and
  (3) a filler such as a polymer or silica,
an adhesive composition comprising
  (1) (meth)acrylic acid ester as a polymerizable monomer,
  (2) a photopolymerization initiator containing camphorquinone as a photosensitizer and N,N-dimethylaminoethyl methacrylate as a reducing agent, and
  (3) a filler such as a polymer or silica, and
an adhesive composition comprising
  (1) (meth)acrylic acid ester as a polymerizable monomer,
  (2) tributylborane partial oxide (TBBO) as a polymerization catalyst, and
  (3) a filler such as a polymer or silica.

For improving the above adhesives in the adhesion to a tooth, it has been proposed to use an adhesion-promoting monomer or a monomer having affinity with a tooth. This adhesion-promoting monomer or monomer having affinity with a tooth includes monomers having a carboxyl group (or a group convertible to a carboxyl group) such as 4-methacryloyloxyethoxycarbonylphthalic acid (4-MET) or its anhydride (4-META) and 10-methacryloyloxydecylmalonic acid (MAC-10), and monomers having a phosphoric acid group such as 10-methacryloyloxydecyl dihydrogenephosphate.

For accomplishing the firm adhesion of these adhesives to a tooth, it is required to carry out the preliminary treatment of the tooth surface. For example, the preliminary treatment that is usually recommended includes a total etching method in which an aqueous solution of phosphoric acid or citric acid is applied simultaneously to the enamel surface and the dentin surface and then, the tooth is washed with water and dried; a total etching primer method in which after the total etching method is carried out, a primer is further applied to the dentin surface and dried; and an enamel etching-dentin primer method in which the enamel alone is etched and then a primer is applied to the remaining dentin without opening dental tubules.

In Journal of Dental Research 63 1087–1089 (1984), Munksgaard and Asmussen E report a method which comprises etching dentin surface with EDTA at pH 7.4, treating the dentin surface with a primer comprising an aqueous solution of 2-hydroxyethyl methacrylate which is a water-soluble monomer, and thereafter applying an adhesive.

U.S. Pat. No. 4,719,149 discloses a primer composition composed of an acid and a water-soluble monomer, which is characterized in that the acid has a pKa between −10 and 10, and the water-soluble monomer is soluble in water up to at least 5% by weight.

And, the primer containing a metal compound is disclosed in JP-A-5-339118, JP-A-6-24928, JP-A-310524 and JP-A-7-89821.

The total etching method or the total etching primer method requires operations comprising many steps of applying an etching agent, washing with water and drying, and further, the dental pulp is attacked by widely opening the dental tubules so that a patient sometimes suffers great pains. In the enamel etching-dentin primer method, it is almost achieved to alleviate pains to a patient, while it is required to apply an etching agent to only an enamel portion in a cavity which is so small and complicated that it is difficult to selectively apply the etching agent there, and the treatment takes a long working time. These problems remain to solve.

It is therefore earnestly desired to develop a primer which can be applied to the simultaneous treatment of enamel and dentin without causing pains on a patient or requiring complicated treatment operations, and which allows an adhesive to exhibit excellent adhesion performance.

It is an object of the present invention to provide a primer composition which can be applied to the simultaneous surface treatment of enamel and dentin of a tooth for overcoming the above problems.

It is another object of the present invention to provide a primer composition, i.e., a tooth surface treating agent, which can be applied to the simultaneous treatment of enamel and dentin in restoring a tooth, which can alleviate pains to a patient with a simple operation without requiring operations of acid treatment or washing with water and which can accomplish an excellent restoring effect.

It is further another object of the present invention to provide a method of forming an adhesive layer on a tooth surface by consecutively applying the primer composition of the present invention and a curable composition to the tooth surface.

According to the present invention, the above objects and advantages of the present invention are achieved, first, by a primer composition for the treatment of a tooth surface, which comprises a) at least one metal compound selected from the group consisting of an iron compound, a copper compound and a cobalt compound, b) a polymerizable monomer having an acidic group, and c) water or water and an organic solvent miscible with water.

In the present invention, the metal compound a) is selected from an iron compound, a copper compound and a cobalt compound. Specific examples of the metal compound preferably include halides such as chlorides and fluorides of the above metals; inorganic acid salts such as nitrates and sulfates of the above metals; organic acid salts such as acetates, acrylates, methacrylates and others of the above metals; and organic complexes such as complexes of acetyl acetone and the above metals. These metal compounds may be those having any valences. Examples of the iron compound include inorganic acid salts such as iron chloride, iron nitrate and iron sulfate, organic acid salts such as iron acetate, iron acrylate and iron methacrylate, and complexes such as iron acetyl acetone. Examples of the copper compound include inorganic acid salts such as copper chloride, copper fluoride, copper nitrate and copper sulfate, organic acid salts such as copper acetate, copper acrylate and copper methacrylate, and complexes such as copper acetyl acetone. Examples of the cobalt compound include inorganic acid salts such as cobalt chloride, cobalt nitrate and cobalt sulfate, organic acid salts such as cobalt acetate, cobalt acrylate and cobalt methacrylate, and complexes such as cobalt acetyl acetone.

These metal compounds may be used alone or in combination.

The content of the metal compound in the primer composition is preferably in the range of from 0.0001 to 1% by weight.

The primer composition of the present invention contains b) a polymerizable monomer having an acidic group. The polymerizable monomer having an acidic group is selected from monomers having a carboxylic acid group and a carboxylic acid anhydride group, monomers having a phosphoric acid group and monomers having a sulfonic acid group.

Examples of the monomers having a carboxylic acid group and a carboxylic acid anhydride group include (meth) acrylic acid and anhydride thereof, 1,4-di(meth) acryloxyethylpyromellitic acid, 6-(meth) acryloxyethylnaphthalene 1,2,6-tricarboxylic acid, N-(meth)acryloyl-p-aminobenzoic acid. N-(meth)acryloyl-o-aminobenzoic acid, N-(meth)acryloyl-m-aminobenzoic acid, N-(meth)acryloyl-5-aminosalicylic acid, N-(meth) acryloyl-4-aminosalicylic acid, 4-(meth) acryloxyethyltrimellitic acid (4-MET) and anhydride (4-META) thereof, 4-(meth)acryloxybutyltrimellitic acid and anhydride thereof, 4-(meth)acryloxyhexyltrimellitic acid and anhydride thereof, 4-(meth) acryloxydecyltrimellitic acid and anhydride thereof, 2-(meth)acryloyloxybenzoic acid, 3-(meth) acryloyloxybenzoic acid, 4-(meth)acryloyloxybenzoic acid, β-(meth)acryloyoxyethyl hydrogensuccinate (β-MEHS), β-(meth)acryloyloxyethyl hydrogenmaleate, β-(meth) acryloyloxyethyl hydrogenphthalate, 11-(meth)acryloyloxy-1,1-undecanedicarboxylic acid, and p-vinylbenzoic acid.

Examples of the monomers having a phosphoric acid group include (2-(meth)acryloxyethyl)phosphoric acid, (2-(meth)acryloxyethylphenyl)phosphoric acid, and 10-(meth) acryloxydecylphosphoric acid.

Examples of the monomers having a sulfonic acid group include p-styrenesulfonic acid and 2-acrylamide-2-methylpropanesulfonic acid.

These polymerizable monomers having an acidic group may be used alone or in combination.

Of these, particularly preferred are N-(meth)acryloyl-5-aminosalicylic acid, N-(meth)acryloyl-4-aminosalicylic acid and 4-(meth)acryloxyethyltrimellitic acid and anhydride thereof.

These polymerizable monomers having an acidic group may be used alone or in combination.

The content of the polymerizable monomer having an acidic group in the primer composition is generally in the range of from 0.1 to 30% by weight.

The primer composition of the present invention contains c) water or water and an organic solvent miscible with water. The above a) specific metal compound and the above b) polymerizable monomer having an acidic group are dissolved or dispersed in water or a combination of water and an organic solvent miscible with water when used. The above solvent can be selected from any of those having no high toxicity to a human body. Examples of the solvent preferably include ethanol, isopropanol, butanol, acetone and tetrahydrofuran. These solvents may be used alone or in combination. For accomplishing effective enamel surface treatment which can attain firm adhesion, the content of the water or the content of the water in the water or the water and the organic solvent miscible with water, as a component c), per 100 parts by weight of the total amount of the components a), b) and c), is preferably at least 40 parts by weight, more preferably at least 45 parts by weight, particularly preferably at least 50 parts by weight.

When the water content is at least 40 parts by weight the demoralization of the enamel surface necessary for adhesion easily takes place, a demineralized apatite component is no longer deposited, and effective adhesion strength can be obtained.

In the primer composition for the treatment of a tooth surface, provided by the present invention, the above a) specific metal compound, the above b) polymerizable monomer having an acidic group and the above c) water or water and organic solvent miscible with water, may be separated to two arbitrary proportions as required, stored and mixed before use when applied to a tooth.

The above primer composition of the present invention is applied to the surface of a tooth. After it is dried, a curable composition is applied onto the dry primer composition to form an adhesive layer, and various materials can be bonded to the tooth. In this case, after the curable composition has been applied, a filler or a restoration material may be laminated as required before the curable composition is cured, so that the filler or the restoration material can be bonded to the tooth owing to the adhesion strength of the curable composition.

The curable composition can be selected from those curable compositions known in the field of this art, while it is particularly preferred to use a curable composition containing trialkylborane or a partial oxide thereof.

According to the present invention, therefore, there is provided a method of forming an adhesive layer on a tooth surface, which comprises applying the primer composition of the present invention to the tooth surface and then applying a curable composition containing a polymerization initiator and a polymerizable monomer.

As described above, the curable composition to be applied onto the primer composition comprises a polymerization initiator and a polymerizable monomer or a polymerizable monomer and a filler. That is, this adhesive tself may be used as an adhesive to bond a filler of a metal, or may be an adhesive as a liner of a composite resin.

The polymerizable monomer used in the curable composition is preferably selected from (meth)acryloyl monomers. Examples of the (meth)acryloyl monomers include monofunctional (meth)acrylates such as methyl (meth)acrylate, ethyl (meth)acrylate, hexyl (meth)acrylate, tetrahydrofurfuryl (meth)acrylate and 2-hydroxyethyl (meth)acrylate, difunctional (meth)acrylates such as ethylene glycol di(meth)acrylate, triethylene glycol di(meth)acrylate, hexamethylene glycol di(meth)acrylate, 2,2-bis[4-methacryloxyethoxy)phenyl]propane and 2,2-bis(4-(methacryloyloxypolyethoxyphenyl)propane, trifunctional or polyfunctional (meth)acrylates such as trimethylolpropane tri(meth)acrylate and pentaerythritol tetra(meth) acrylate, and (meth)acryloyl compounds containing an acid group such as 4-methacryloyloxyethoxycarbonylphthalic acid and anhydride thereof, 5-methacryloylaminosalicylic acid and 10-methacryloyloxydecyl dihydrogenphosphate. These polymerizable monomers may be used alone or in combination.

The polymerization initiator used in the curable composition includes organic peroxide, inorganic peroxide, alkylborane, partially oxidized alkylborane, an α-diketone compound, an organic amine compound, organic sulfinic acid, organic sulfinic acid salt, an inorganic sulfur compound and barbituric acids. The above polymerization initiators may be used alone or in combination. The above polymerization initiators can be grouped into a type for room temperature chemical polymerization, a type for photopolymerization and a dual type for a combination of the above polymerizations. The peroxide (polymerization initiator) which is used as a type for room temperature chemical polymerization includes organic peroxides such as diacetyl peroxide, dipropyl peroxide, dibutyl peroxide, dicapryl peroxide, dilauryl peroxide, benzoyl peroxide (BPO), p,p'-dichlorobenzoyl peroxide, p,p'-dimethoxybenzoyl peroxide, p,p'-dimethylbenzoyl peroxide and p,p'-dinitrobenzoyl peroxide and inorganic peroxides such as ammonium persulfate, potassium persulfate, potassium chlorate, potassium bromate and potassium perphosphate. Of these, BPO is preferred.

The polymerization initiator which is used as a type for the photopolymerization is a polymerization initiator with which the polymerization can be carried out by irradiating the composition with ultraviolet light or visible light. The polymerization initiator used for the above photopolymerization is not specially limited. The above polymerization initiator includes ultraviolet light or visible light sensitizers such as α-diketone compounds including benzil, 4,4'-dichlorobenzil, benzoin, benzoin methyl ether, benzoin ethyl ether, benzoin isopropyl ether, benzophenone, 9,10-anthraquinone, diacetyl and d,l-camphorquinone (CQ).

When the polymerization is carried out in the presence of a polymerization initiator which is a type for room temperature chemical polymerization or photopolymerization, a reducing compound may be used in combination. The organic reducing compound includes aromatic amines such as N,N-dimethylanlline, N,N-dimethyl p-toluidine (DMPT), N,N-diethyl p-toluidine, N,N-diethanol p-toluidine (DEPT), N,N-dimethyl p-tertbutylaniline, N,N-dimethylanisidine, N,N-dimethyl p-chloroaniline, N,N-dimethylaminoethyl (meth)acrylate, N,N-diethylaminoethyl (meth)acrylate, N,N-dimethylaminobenzoic acid and alkyl ester thereof, N,N-diethylaminobenzoic acid (DEABA) and alkyl ester thereof and N,N-dimethylaminobenzaldehyde (DMABAd); N-phenylglycine (NPG), N-tolylglycine (NTG) and N,N-(3-methacryloyloxy-2-hydroxypropyl)phenylglycine (NPG-GMA).

Of the above reducing compounds, preferred are DMPT, DEPT, DEABA, DMABAd, NPG and NTG.

Further, for reliably curing and improving the curable composition in adhesion to a tooth, it is preferred to incorporate at least one of amine compounds of the formula (I),

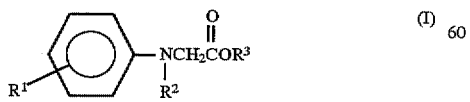

wherein each of $R^1$ and $R^2$ is independently a hydrogen atom or an alkyl group which may contain a functional group or a substituent, and $R^3$ is a hydrogen atom or metal, and of the formula (II),

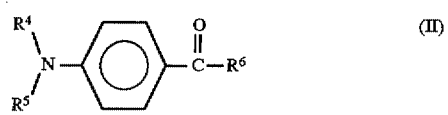

wherein each of $R^4$ and $R^5$ is independently a hydrogen atom or an alkyl group, and $R^6$ is a hydrogen atom, OH an alkyl group which may contain a functional group or a substituent or an alkoxyl group which may contain a functional group or a substituent.

The amine compound coming under the formula (I) includes NPG, NTG and NPG-GMA which are already described. NPG is particularly preferred. The amine compound of the formula (II) includes, in addition to N,N-dimethylaminobenzoic acid and alkyl ester thereof and N,N-diethylaminobenzoic acid (DEABA) and alkyl ester thereof, which are already described, aliphatic alkylaminobenzoic acids and alkyl esters thereof typified by N,N-dipropylaminobenzoic acid and alkyl ester thereof, N-isopropylaminobenzoic acid and alkyl ester thereof and N-isopropyl-N-methylaminobenzoic acid and alkyl ester thereof; aliphatic alkylaminobenzoaldehydes typified by DMABAd, N,N-diethylaminobenzoaldehyde, N,N-dipropylaminobenzoaldehyde and N-isopropyl-N-methylaminobenzaldehyde; aliphatic alkylaminoacetylbenzenes typified by N,N-dimethylaminoacetylbenzene, N,N-diethylaminoacetylbenzene, N,N-dipropylaminoacetylbenzene, N-isopropylaminoacetylbenzene and N-isopropyl-N-methylaminoacetylbenzene and aliphatic alkylaminoacylbenzenes. These amine compounds may be used alone or in combination.

In addition to the above compounds, the reducing compound includes aromatic sulfinic acids such as benzenesulfinic acid, o-toluenesulfinic acid, ethylbenzenesulfinic acid, decylbenzenesulfinic acid, dodecylbenzenesulfinic acid, chlorobenzenesulfinic acid and naphthalenesulfinic acid and salts thereof.

The inorganic reducing compound is preferably selected from sulfur-containing, reducing inorganic compounds. These compounds are preferably reducing inorganic compounds used as redox initiators which can be used for polymerizing a radical-polymerizable monomer in a solvent such as water or a water-containing solvent. Examples thereof include sulfurous acid, bisulfurous acid, metasulfurous acid, metabisulfurous acid, pyrosulfurous acid, thiosulfurous acid, dithionous acid, dithionic acid, hyposulfurous acid, hydrosulfurous acid and salts of these. Of these, sulfites are preferred, and particularly preferred are sodium sulfite, potassium sulfite, sodium hydrogensulfite and potassium hydrogensulfite. These reducing inorganic compounds may be used alone or in combination.

Further, examples of the filler used in the curable composition include powders of polymers such as polymethyl methacrylate, a glass powder, and powders of metal oxides such as zirconium oxide, and these may be used alone or in combination.

EXAMPLES

The present invention will be explained with reference to Examples hereinafter while the present invention shall not be limited to these Examples.

Examples 1–14

A bovine anterior tooth on a lip side was cut to expose a surface of enamel and/or dentin, and the surface of enamel or dentin was polished with No. 600 emery paper with water-pouring to prepare an adhesion surface.

The above adhesion surface was washed with water and dried. Then, a primer solution of a metal salt and an acidic monomer shown in Table 1 was applied, and after 30 seconds, it was dried by air-blowing it with an air gun. Then, a Cellophane tape having a hole having a diameter of 5 mm was attached to the adhesion surface to define an adhesion area.

Then, a liquid (curable composition) prepared by incorporating 30 parts by weight of tributylborane partial oxide (TBBO: supplied by Sun Medical Co., Ltd) as a polymerization initiator to a mixture containing 50 parts by weight of methyl methacrylate (Wako special grade, supplied by Wako Purechemical Industries, Ltd.), 30 parts by weight of 2,2-bis[4-(methacryloxyethoxy)phenyl]propane (NK Ester D-2.6E, supplied by Shin Nakamura Chemical Co., Ltd.), 15 parts by weight of 2-hydroxyethyl methacrylate (Wako special grade, supplied by Wako Purechemical Industries, Ltd.) and 5 parts by weight of 4-methacryloxyethyltrimellitic acid anhydride (supplied by Sun Medical Co., Ltd) was applied to the above primer, and the applied surface was moderately air-blown so that the curable composition was spread to form a uniform coating.

The coating was allowed to stand for 30 seconds, and a 1 mm thick Teflon mold having a hole with a diameter of 5 mm was attached to the adhesion surface. A composite resin for dental treatment (Silax Plus, supplied by 3M) was filled in the hole portion, and irradiated with visible light with a visible light irradiator for dental treatment (Translux, supplied by Kulzer) at a distance of 5 mm for 60 seconds to cure the composite resin.

A rod of polymethyl methacrylate (PMMA) was bonded onto the cured composite resin with a fast-curable immediately-polymerizable resin (Metafast, supplied by Sun Medical Co., Ltd) to prepare an adhesion test sample.

The adhesion test sample was allowed to stand at room temperature for 30 minutes, immersed in distilled water at 37° C. for 24 hours and subjected to a tensile test for an adhesion strength between the PMMA rod and the tooth. The adhesion strength is an average of measurement values of five samples.

Table 1 shows the adhesion strength measured in the above manner.

TABLE 1

| | Composition (part by weight) | | | Adhesion |
|---|---|---|---|---|
| | Solvent | Metal compound | Monomer having acidic group | strength (MPa) |
| Ex. 1 | Water: 50 Ethanol 35 | Ferric chloride: 0.1 | 4-META: 15 | E: 11.2 D: 15.6 |
| Ex. 2 | Water: 50 Ethanol 35 | Ferric chloride: 0.05 | 4-META: 15 | E: 12.1 D: 16.2 |
| Ex. 3 | Water: 45 Ethanol 40 | Ferric chloride: 0.05 | 4-META: 15 | E: 9.5 D: 15.2 |
| Ex. 4 | Water: 40 Ethanol 45 | Ferric chloride: 0.05 | 4-META: 15 | E: 7.7 D: 14.7 |
| Ex. 5 | Water: 55 Ethanol 35 | Ferric chloride: 0.05 | 4-META: 10 | E: 10.7 D: 14.5 |
| Ex. 6 | Water: 60 Ethanol 35 | Ferric nitrate: 0.1 | 4-META: 5 | E: 9.5 D: 13.2 |
| Ex. 7 | Water: 55 Ethanol 35 | Ferric nitrate: 0.1 | 4-META: 10 | E: 10.3 D: 14.8 |
| Ex. 8 | Water: 55 Ethanol 30 | Ferric nitrate: 0.1 | 4-META: 15 | E: 11.9 D: 15.8 |
| Ex. 9 | Water: 55 Ethanol 35 | Ferric nitrate: 0.05 | 4-META: 10 | E: 11.8 D: 16.1 |

TABLE 1-continued

| | Composition (part by weight) | | | Adhesion |
|---|---|---|---|---|
| | Solvent | Metal compound | Monomer having acidic group | strength (MPa) |
| Ex. 10 | Water: 55 Ethanol 30 | Ferric nitrate: 0.1 | 4-META: 15 | E: 11.5 D: 15.4 |
| Ex. 11 | Water: 55 Ethanol 35 | Ferric nitrate: 0.1 | β-MEHS: 10 | E: 10.8 D: 14.4 |
| Ex. 12 | Water: 55 Ethanol 30 | Ferric nitrate: 0.1 | 4-META: 15 | E: 11.0 D: 13.4 |
| Ex. 13 | Water: 55 Ethanol 30 | Ferric chloride: 0.05 | 4-META: 15 | E: 10.7 D: 13.5 |
| Ex. 14 | Water: 55 Ethanol 30 | Ferric nitrate: 0.05 | 4-META: 15 | E: 12.9 D: 15.8 |

Ex. = Example

Abbreviations used in Table 1 refer to the following compounds.

4-META: 4-methacryloxyethyltrimellitic acid anhydride (supplied by Sun Medical Co., Ltd)

β-MEHS: β-methacryloyloxyethyl hydrogensuccinate (NK Ester SA, supplied by Shin Nakamura Chemical Co., Ltd.)

Comparative Examples 1–7

A PMMA rod was bonded to the adhesion surface of a bovine tooth in the same manner as in Example 1 except that the primer solution was replaced with a primer solution having a composition shown in Table 2.

Table 2 shows the adhesion strength.

TABLE 2

| | Composition (part by weight) | | | Adhesion |
|---|---|---|---|---|
| | Solvent | Metal compound | Monomer having acidic group | strength (MPa) |
| CEx. 1 | Water: 60 Ethanol 40 | 0 | 0 | E: 0.5 D: 0.8 |
| CEx. 2 | Water: 60 Ethanol 40 | Ferric chloride: 0.1 | 0 | E: 0.6 D: 6.2 |
| CEx. 3 | Water: 60 Ethanol 40 | Ferric nitrate: 0.1 | 0 | E: 0.5 D: 7.5 |
| CEx. 4 | Water: 55 Ethanol 30 | 0 | 4-META: 15 | E: 8.5 D: 3.5 |
| CEx. 5 | Water: 25 Ethanol 70 | Ferric nitrate: 0.1 | 4-META: 5 | E: 3.7 D: 9.5 |
| CEx. 6 | Water: 25 Ethanol 65 | Ferric nitrate: 0.1 | 4-META: 10 | E: 6.0 D: 10.2 |
| CEx. 7 | Water: 35 Ethanol 50 | Ferric nitrate: 0.05 | 4-META: 15 | E: 5.8 D: 13.2 |

CEx. = Comparative Example

Effect of the Invention

According to the present invention, both the enamel and the dentin of a tooth can be simultaneously surface-treated without acid treatment or washing with water, and adhesion dental treatment can be reliably carried out by a simple operation without causing pains on a patient.

What is claimed is:

1. A primer composition for the treatment of a tooth surface, which consists essentially of at least one metal compound selected from the group consisting of an iron compound, a copper compound and a cobalt compound, b) a polymerizable monomer having an acid group, and c) water or water and an organic solvent miscible with water, wherein said water or water in the water and organic solvent is in an amount of at least 40 parts by weight per 100 parts by weight of the total amount of components a), b) and c).

2. The primer composition of claim 1, wherein the metal compound has a concentration in the range of from 0.0001 to 1% by weight.

3. The primer composition of claim 1, wherein the monomer having an acidic group has a concentration in the range of from 0.1 to 30% by weight.

4. The primer composition of claim 1, wherein the primer composition is stored by separating the components a), b) and c) to two arbitrary proportions.

5. A method of forming an adhesive layer on a tooth surface, which comprises applying the primer composition of claim 1 to the tooth surface and then applying a curable composition containing trialkylborane or partial oxide thereof and a polymerizable monomer.

6. A primer composition for the treatment of a tooth surface, which comprises a) at least one metal compound selected from the group consisting of an iron compound, a copper compound and a cobalt compound, b) a polymerizable monomer consisting of a polymerizable monomer having an acidic group and c) water or water and an organic solvent miscible with water, wherein said water or water in the water and organic solvent is in an amount of at least 40 parts by weight per 100 parts by weight of the total amount of components a), b) and c).

7. A primer composition for the treatment of a tooth surface, which consists essentially of a) at least one metal compound selected from the group consisting of an iron compound, a copper compound and a cobalt compound, b) a polymerizable monomer having an acidic group selected from the group consisting of carboxylic acid and anhydride group, phosphoric acid group and sulfonic acid group, and c) water or water and an organic solvent miscible with water, wherein said water or water in the water and organic solvent is in an amount of at least 40 parts by weight per 100 parts by weight of the total amount of components a), b) and c).

8. The primer composition of claim 7 wherein said polymerizable monomer having an acidic group is a member selected from the group consisting of (2-(meth)acryloxyethyl)phosphoric acid, p-styrenesulfonic acid and 4-(meth)-acryloxyethyltrimellitic acid and anhydride.

9. The primer composition of claim 7, wherein the metal compound has a concentration in the range of from 0.05 to 1% by weight.

10. The primer composition of claim 7, wherein the monomer having an acidic group has a concentration in the range of from 5.0 to 30% by weight.

11. A method of forming an adhesive layer on a tooth surface, which comprises applying the primer composition of claim 7 to the tooth surface and then applying a curable composition containing trialkylborane or partial oxide thereof and a polymerizable monomer.

12. A primer composition for the treatment of a tooth surface, which consists essentially of a) at least one metal compound, in an amount of 0.05 to 1% by weight, selected from the group consisting of an iron compound, a copper compound and a cobalt compound, b) a polymerizable monomer having an acidic group, in an amount of 5.0 to 30% by weight, selected from the group consisting of N-(meth)acryloyl-5-aminosalicylic acid, N-(meth)acryloyl-4-aminosalicylic acid and 4(meth)acryloxyethyltrimellitic acid and anhydride and β-(meth)acryloyoxyethyl hydrogensuccinate, and c) water or water and an organic solvent miscible with water, wherein said water or water in the water and organic solvent is in an amount of at least 40 parts by weight per 100 parts by weight of the total amount of components a), b) and c).

13. The primer composition of claim 12, wherein the polymerizable monomer having an acidic group consists essentially of N-(meth)acryloyl-5-aminosalicylic acid.

14. The primer composition of claim 12 wherein the polymerizable monomer having an acidic group consists essentially of N-(meth)acryloyl-4-aminosalicylic acid.

15. The primer composition of claim 12 wherein the polymerizable monomer having an acidic group consists essentially of 4(meth)acryloxyethyltrimellitic acid and anhydride.

16. The primer composition of claim 12 wherein the polymerizable monomer having an acidic group consists essentially of B-(meth)acryloyoxyethyl hydrogensuccinate.

17. A method of forming an adhesive layer on a tooth surface, which comprises applying the primer composition of claim 12 to the tooth surface an then applying a curable composition containing trialkylborane or partial oxide thereof and a polymerizable monomer.

* * * * *